(12) United States Patent
Oft et al.

(10) Patent No.: US 7,282,204 B2
(45) Date of Patent: Oct. 16, 2007

(54) USES OF IL-23 AGONISTS AND ANTAGONISTS; RELATED REAGENTS

(75) Inventors: Martin Oft, Palo Alto, CA (US); Terrill K. McClanahan, Sunnyvale, CA (US)

(73) Assignee: Schering Corporation, Kenilworth, NJ (US)

(*) Notice: Subject to any disclaimer, the term of this patent is extended or adjusted under 35 U.S.C. 154(b) by 210 days.

(21) Appl. No.: 10/797,157

(22) Filed: Mar. 9, 2004

(65) Prior Publication Data

US 2004/0223969 A1 Nov. 11, 2004

Related U.S. Application Data

(60) Provisional application No. 60/453,672, filed on Mar. 10, 2003.

(51) Int. Cl.
    *A61K 39/00* (2006.01)
(52) U.S. Cl. .................. 424/139.1; 424/141.1; 530/351
(58) Field of Classification Search .................. None
    See application file for complete search history.

(56) References Cited

U.S. PATENT DOCUMENTS

2003/0157105 A1* 8/2003 Carton et al. ............ 424/145.1

FOREIGN PATENT DOCUMENTS

| WO | WO 01/18051 A2 | 3/2001 |
|----|----------------|--------|
| WO | WO 01/85790 A2 | 11/2001 |
| WO | WO 02/29060 A2 | 4/2002 |
| WO | WO 02/097048 A2 | 12/2002 |

OTHER PUBLICATIONS

DeJong et al., A single cDNA, hTFIIA/alpha, encodes both the p35 and p19 subunits of human TFIIA. Genes Dev., 1993, 7(11):2220-34, (abstract only).*
Broberg, et al. (2002) *J. Interferon Cytokine Res.* 22:641-651 "Herpes Simplex Virus Type 1 Infection Induces Upregulation of Interleukin-23 (p19) mRNA Expression in Trigeminal Ganglia of BALB/c Mice".
Cannistra and Niloff (1996) *New Engl. J. Med.* 334:1030-1038 "Cancer of the Uterine Cervix".
Cooper, et al. (2002) *J. Immunol.* 168:1322-1327 "Mice Lacking Bioactive IL-12 Can Generate Protective, Antigen-Specific Cellular Responses to Mycobacterial Infection Only if the IL-12 p40 Subunit Is Present".
Cua, et al. (2003) *Nature* 421:744-748 "Interleukin-23 rather than interleukin-12 is the critical cytokine for autoimmune inflammation of the brain".
Elkins, et al. (2002) *Infection Immunity* 70:1936-1948 "In Vivo Clearance of an Intracellular Bacterium, *Francisella tulatensis* LVS, Is Dependent on the p40 Subunit of Interleukin-12 (IL-12) but Not on IL-12 p70".

Enzinger and Mayer (2003) *New Engl. J. Med.* 349:2241-2252 "Esophageal Cancer".
Farrar, et al. (1999) *J. Immunol.* 162:2842-2849 "Cancer Dormancy. VII. A Regulatory Role for CD8+ T Cells and IFN-y in Establishing and Maintaining the Tumor-Dormant State".
Fischer, et al. (1997) *Nature Biotechnol.* 15:142-145 "A bioactive designer cytokine for human hematopoietic progenitor cell expansion".
Forastiere, et al. (2001) *New Engl. J. Med.* 345:1890-1900 "Head and Neck Cancer".
Frucht (2002) *Sci STKE* 2002, E1-E3 "IL-23: A Cytokine That Acts on Memory T Cells".
Izbicki, et al. (1997) *New Engl. J. Med.* 337:1188-1194 "Prognostic Value of Immunohistochemically Identifiable Tumor Cells in Lymph Nodes of Patients with Completely Resected Esophageal Cancer".
Le, et al. (2001) *J. Immunol.* 167:6765-6772 "Pre-Existing Tumor-Sensitized T Cells Are Essential for Eradication of Established Tumors by IL-12 and Cyclophosphamide Plus IL-12".
Lynch and Chapelle (2003) *New Engl. J. Med.* 348:919-932 "Hereditary Colorectal Cancer".
Oppmann, et al. (2000) *Immunity* 13:715-725 "Novel p19 Protein Engages IL-12p40 to Form a Cytokine, IL-23, with Biological Activities Similar as Well as Distinct from IL-12".
Osborne (1998) *New Engl. J. Med.* 339:1609-1618 "Tamoxifen In the Treatment of Breast Cancer".
Parham, et al. (2002) *J. Immunol.* 168:5699-5708 "A Receptor for the Heterodimeric Cytokine IL-23 Is Composed of IL-12Rβ1 and a Novel Cytokine Receptor Subunit, IL-23R".
Peters, et al.(1998) *J. Immunol.* 161:3575-3581 "In Vivo and In Vitro Activities of the gp130-Stimulating Designer Cytokine Hyper-IL-6".
Pirhonen, et al. (2002) *J. Immunol.* 169:5673-5678 "Regulation of Virus-Induced IL-12 and IL-23 Expression in Human Macrophages".
Rakemann, et al. (1999) *J. Biol. Chem.* 274:1257-1266 "The Designer Cytokine Hyper-Interleukin-6 Is a Potent Activator of STAT3-dependent Gene Transcription in Vivo and in Vitro".
Ramirez-Montagut, et al. (2003) *Oncogene* 22:3180-3187 "Immunity to melanoma: unraveling the relation of tumor immunity and autoimmunity".
Sawaya, et al. (2003) *New Engl. J. Med.* 349:1501-1509 "Risk of Cervical Cancer Associated with Extending the Interval between Cervical-Cancer Screenings".
Wiekowski, et al. (2001) *J. Immunol.* 166:7563-7570 "Ubiquitous Transgenic Expression of the IL-23 Subunit p19 Induces Multiorgan Inflammation, Runting, Infertility, and Premature Death".

(Continued)

*Primary Examiner*—Gary B. Nickol
*Assistant Examiner*—Dong Jiang
(74) *Attorney, Agent, or Firm*—Sheela Mohan-Peterson; Gregory R. Bellomy

(57) ABSTRACT

Provided are methods of treatment for tumors. In particular, methods are provided for modulating activity of a cytokine molecule and its receptor.

11 Claims, No Drawings

OTHER PUBLICATIONS

Ugai, et al. (2003) *Cancer Gene Therapy* 10:771-778 "Transduction of the IL-21 and IL-23 genes in human pancreatic carcinoma cells produces natural killer cell-dependent and -independent antitumor effects".

Lo, et al. (2003) *J. Immunol.* 171:600-607 "Antitumor and Antimetastatic Activity of IL-23".

Coussens and Werb, Insight review articles: Inflammation and cancer, Nature (2002), vol. 420, pp. 860-867.

* cited by examiner

SEQUENCE LISTING

```
<160> NUMBER OF SEQ ID NOS: 11

<210> SEQ ID NO 1
<211> LENGTH: 570
<212> TYPE: DNA
<213> ORGANISM: Homo sapiens
<220> FEATURE:
<221> NAME/KEY: CDS
<222> LOCATION: (1)..(567)
<220> FEATURE:
<221> NAME/KEY: mat_peptide
<222> LOCATION: (64)..(567)

<400> SEQUENCE: 1 atg ctg ggg agc aga gct gta atg ctg ctg ttg ctg ctg ccc tgg aca      48
Met Leu Gly Ser Arg Ala Val Met Leu Leu Leu Leu Leu Pro Trp Thr
    -20                 -15                 -10 gct cag ggc aga gct gtg cct ggg ggc agc agc cct gcc tgg act cag      96
Ala Gln Gly Arg Ala Val Pro Gly Gly Ser Ser Pro Ala Trp Thr Gln
-5              -1  1               5                   10 tgc cag cag ctt tca cag aag ctc tgc aca ctg gcc tgg agt gca cat     144
Cys Gln Gln Leu Ser Gln Lys Leu Cys Thr Leu Ala Trp Ser Ala His
                15                  20                  25 cca cta gtg gga cac atg gat cta aga gaa gag gga gat gaa gag act     192
Pro Leu Val Gly His Met Asp Leu Arg Glu Glu Gly Asp Glu Glu Thr
            30                  35                  40 aca aat gat gtt ccc cat atc cag tgt gga gat ggc tgt gac ccc caa     240
Thr Asn Asp Val Pro His Ile Gln Cys Gly Asp Gly Cys Asp Pro Gln
        45                  50                  55 gga ctc agg gac aac agt cag ttc tgc ttg caa agg atc cac cag ggt     288
Gly Leu Arg Asp Asn Ser Gln Phe Cys Leu Gln Arg Ile His Gln Gly
60                  65                  70                  75 ctg att ttt tat gag aag ctg cta gga tcg gat att ttc aca ggg gag     336
Leu Ile Phe Tyr Glu Lys Leu Leu Gly Ser Asp Ile Phe Thr Gly Glu
                80                  85                  90 cct tct ctg ctc cct gat agc cct gtg gcg cag ctt cat gcc tcc cta     384
Pro Ser Leu Leu Pro Asp Ser Pro Val Ala Gln Leu His Ala Ser Leu
            95                  100                 105 ctg ggc ctc agc caa ctc ctg cag cct gag ggt cac cac tgg gag act     432
Leu Gly Leu Ser Gln Leu Leu Gln Pro Glu Gly His His Trp Glu Thr
        110                 115                 120 cag cag att cca agc ctc agt ccc agc cag cca tgg cag cgt ctc ctt     480
Gln Gln Ile Pro Ser Leu Ser Pro Ser Gln Pro Trp Gln Arg Leu Leu
    125                 130                 135 ctc cgc ttc aaa atc ctt cgc agc ctc cag gcc ttt gtg gct gta gcc     528
Leu Arg Phe Lys Ile Leu Arg Ser Leu Gln Ala Phe Val Ala Val Ala
140                 145                 150                 155 gcc cgg gtc ttt gcc cat gga gca gca acc ctg agt ccc taa             570
Ala Arg Val Phe Ala His Gly Ala Ala Thr Leu Ser Pro
                160                 165

<210> SEQ ID NO 2
<211> LENGTH: 189
<212> TYPE: PRT
<213> ORGANISM: Homo sapiens

<400> SEQUENCE: 2
```

```
Met Leu Gly Ser Arg Ala Val Met Leu Leu Leu Leu Pro Trp Thr
    -20                 -15                 -10

Ala Gln Gly Arg Ala Val Pro Gly Gly Ser Ser Pro Ala Trp Thr Gln
 -5              -1   1               5                      10

Cys Gln Gln Leu Ser Gln Lys Leu Cys Thr Leu Ala Trp Ser Ala His
             15                  20                  25

Pro Leu Val Gly His Met Asp Leu Arg Glu Glu Gly Asp Glu Thr
         30                  35                  40

Thr Asn Asp Val Pro His Ile Gln Cys Gly Asp Gly Cys Asp Pro Gln
         45                  50                  55

Gly Leu Arg Asp Asn Ser Gln Phe Cys Leu Gln Arg Ile His Gln Gly
 60              65                  70                      75

Leu Ile Phe Tyr Glu Lys Leu Leu Gly Ser Asp Ile Phe Thr Gly Glu
                 80                  85                  90

Pro Ser Leu Leu Pro Asp Ser Pro Val Ala Gln Leu His Ala Ser Leu
             95                  100                 105

Leu Gly Leu Ser Gln Leu Leu Gln Pro Glu Gly His His Trp Glu Thr
            110                 115                 120

Gln Gln Ile Pro Ser Leu Ser Pro Ser Gln Pro Trp Gln Arg Leu Leu
            125                 130                 135

Leu Arg Phe Lys Ile Leu Arg Ser Leu Gln Ala Phe Val Ala Val Ala
140                 145                 150                 155

Ala Arg Val Phe Ala His Gly Ala Ala Thr Leu Ser Pro
                160                 165

<210> SEQ ID NO 3
<211> LENGTH: 1203
<212> TYPE: DNA
<213> ORGANISM: Mus musculus
<220> FEATURE:
<221> NAME/KEY: CDS
<222> LOCATION: (113)..(700)
<220> FEATURE:
<221> NAME/KEY: mat_peptide
<222> LOCATION: (176)..(700)

<400> SEQUENCE: 3
cgcttagaag tcggactaca gagttagact cagaaccaaa ggaggtggat aggggggtcca      60 caggcctggt gcagatcaca gagccagcca gatctgagaa gcagggaaca ag atg ctg     118
                                                         Met Leu
                                                            -20
gat tgc aga gca gta ata atg cta tgg ctg ttg ccc tgg gtc act cag      166
Asp Cys Arg Ala Val Ile Met Leu Trp Leu Leu Pro Trp Val Thr Gln
        -15                 -10                  -5 ggc ctg gct gtg cct agg agt agc agt cct gac tgg gct cag tgc cag      214
Gly Leu Ala Val Pro Arg Ser Ser Ser Pro Asp Trp Ala Gln Cys Gln
     -1   1               5                  10 cag ctc tct cgg aat ctc tgc atg cta gcc tgg aac gca cat gca cca      262
Gln Leu Ser Arg Asn Leu Cys Met Leu Ala Trp Asn Ala His Ala Pro
         15                  20                  25 gcg gga cat atg aat cta cta aga gaa gaa gag gat gaa gag act aaa      310
Ala Gly His Met Asn Leu Leu Arg Glu Glu Glu Asp Glu Glu Thr Lys
 30                  35                  40                  45 aat aat gtg ccc cgt atc cag tgt gaa gat ggt tgt gac cca caa gga      358
Asn Asn Val Pro Arg Ile Gln Cys Glu Asp Gly Cys Asp Pro Gln Gly
                 50                  55                  60 ctc aag gac aac agc cag ttc tgc ttg caa agg atc cgc caa ggt ctg      406
Leu Lys Asp Asn Ser Gln Phe Cys Leu Gln Arg Ile Arg Gln Gly Leu
             65                  70                  75
```

```
gct ttt tat aag cac ctg ctt gac tct gac atc ttc aaa ggg gag cct       454
Ala Phe Tyr Lys His Leu Leu Asp Ser Asp Ile Phe Lys Gly Glu Pro
        80                  85                  90 gct cta ctc cct gat agc ccc atg gag caa ctt cac acc tcc cta cta       502
Ala Leu Leu Pro Asp Ser Pro Met Glu Gln Leu His Thr Ser Leu Leu
    95                 100                 105 gga ctc agc caa ctc ctc cag cca gag gat cac ccc cgg gag acc caa       550
Gly Leu Ser Gln Leu Leu Gln Pro Glu Asp His Pro Arg Glu Thr Gln
110                 115                 120                 125 cag atg ccc agc ctg agt tct agt cag cag tgg cag cgc ccc ctt ctc       598
Gln Met Pro Ser Leu Ser Ser Ser Gln Gln Trp Gln Arg Pro Leu Leu
            130                 135                 140 cgt tcc aag atc ctt cga agc ctc cag gcc ttt ttg gcc ata gct gcc       646
Arg Ser Lys Ile Leu Arg Ser Leu Gln Ala Phe Leu Ala Ile Ala Ala
                145                 150                 155 cgg gtc ttt gcc cac gga gca gca act ctg act gag ccc tta gtg cca       694
Arg Val Phe Ala His Gly Ala Ala Thr Leu Thr Glu Pro Leu Val Pro
    160                 165                 170 aca gct taaggatgcc caggttccca tggctaccat gataagacta atctatcagc        750
Thr Ala
    175 ccagacatct accagttaat taacccatta ggacttgtgc tgttcttgtt tcgtttgttt     810 tgcgtgaagg gcaaggacac cattattaaa gagaaaagaa acaaaccccca gagcaggcag    870 ctggctagag aaaggagctg gagaagaaga ataaagtctc gagcccttgg ccttggaagc     930 gggcaagcag ctgcgtggcc tgaggggaag ggggcggtgg catcgagaaa ctgtgagaaa     990 acccagagca tcagaaaaag tgagcccagg ctttggccat tatctgtaag aaaaacaaga    1050 aaagggggaac attatacttt cctgggtggc tcagggaaat gtgcagatgc acagtactcc   1110 agacagcagc tctgtacctg cctgctctgt ccctcagttc taacagaatc tagtcactaa   1170 gaactaacag gactaccaat acgaactgac aaa                                 1203

<210> SEQ ID NO 4
<211> LENGTH: 196
<212> TYPE: PRT
<213> ORGANISM: Mus musculus

<400> SEQUENCE: 4

Met Leu Asp Cys Arg Ala Val Ile Met Leu Trp Leu Leu Pro Trp Val
        -20                 -15                 -10

Thr Gln Gly Leu Ala Val Pro Arg Ser Ser Pro Asp Trp Ala Gln
-5              -1   1               5                  10

Cys Gln Gln Leu Ser Arg Asn Leu Cys Met Leu Ala Trp Asn Ala His
            15                  20                  25

Ala Pro Ala Gly His Met Asn Leu Leu Arg Glu Glu Asp Glu Glu
        30                  35                  40

Thr Lys Asn Asn Val Pro Arg Ile Gln Cys Glu Asp Gly Cys Asp Pro
    45                  50                  55

Gln Gly Leu Lys Asp Asn Ser Gln Phe Cys Leu Gln Arg Ile Arg Gln
60                  65                  70                  75

Gly Leu Ala Phe Tyr Lys His Leu Leu Asp Ser Asp Ile Phe Lys Gly
                80                  85                  90

Glu Pro Ala Leu Leu Pro Asp Ser Pro Met Glu Gln Leu His Thr Ser
                    95                 100                 105

Leu Leu Gly Leu Ser Gln Leu Leu Gln Pro Glu Asp His Pro Arg Glu
            110                 115                 120
```

```
Thr Gln Gln Met Pro Ser Leu Ser Ser Gln Gln Trp Gln Arg Pro
    125                 130                 135

Leu Leu Arg Ser Lys Ile Leu Arg Ser Leu Gln Ala Phe Leu Ala Ile
140                 145                 150                 155

Ala Ala Arg Val Phe Ala His Gly Ala Ala Thr Leu Thr Glu Pro Leu
                160                 165                 170

Val Pro Thr Ala
            175

<210> SEQ ID NO 5
<211> LENGTH: 2859
<212> TYPE: DNA
<213> ORGANISM: Homo sapiens
<220> FEATURE:
<221> NAME/KEY: CDS
<222> LOCATION: (119)..(2005)
<220> FEATURE:
<221> NAME/KEY: mat_peptide
<222> LOCATION: (188)..(2005)

<400> SEQUENCE: 5
gtggtacggg aattccattg tgttgggcag ccaacaaggg tggcagcctg gctctgaagt      60
ggaattatgt gcttcaaaca ggttgaaaga gggaaacagt cttttcctgc ttccagac      118 atg aat cak gtc act att caa tgg gat gca gta ata gcc ctt tac ata     166
Met Asn Xaa Val Thr Ile Gln Trp Asp Ala Val Ile Ala Leu Tyr Ile
        -20                 -15                 -10 ctc ttc agc tgg tgt cat gga gga att aca aat ata aac tgc tct ggc     214
Leu Phe Ser Trp Cys His Gly Gly Ile Thr Asn Ile Asn Cys Ser Gly
        -5              -1   1               5 cac atc tgg gta gaa cca gcc aca att ttt aag atg ggt atg aat atc     262
His Ile Trp Val Glu Pro Ala Thr Ile Phe Lys Met Gly Met Asn Ile
10                  15                  20                  25 tct ata tat tgc caa gca gca att aag aac tgc caa cca agg aaa ctt     310
Ser Ile Tyr Cys Gln Ala Ala Ile Lys Asn Cys Gln Pro Arg Lys Leu
                30                  35                  40 cat ttt tat aaa aat ggc atc aaa gaa aga ttt caa atc aca agg att     358
His Phe Tyr Lys Asn Gly Ile Lys Glu Arg Phe Gln Ile Thr Arg Ile
            45                  50                  55 aat aaa aca aca gct cgg ctt tgg tat aaa aac ttt ctg gaa cca cat     406
Asn Lys Thr Thr Ala Arg Leu Trp Tyr Lys Asn Phe Leu Glu Pro His
60                  65                  70 gct tct atg tac tgc act gct gaa tgt ccc aaa cat ttt caa gag aca     454
Ala Ser Met Tyr Cys Thr Ala Glu Cys Pro Lys His Phe Gln Glu Thr
        75                  80                  85 ctg ata tgt gga aaa gac att tct tct gga tat ccg cca gat att cct     502
Leu Ile Cys Gly Lys Asp Ile Ser Ser Gly Tyr Pro Pro Asp Ile Pro
90                  95                  100                 105 gat gaa gta acc tgt gtc att tat gaa tat tca ggc aac atg act tgc     550
Asp Glu Val Thr Cys Val Ile Tyr Glu Tyr Ser Gly Asn Met Thr Cys
                110                 115                 120 acc tgg aat gct rgg aag ctc acc tac ata gac aca aaa tac gta gta     598
Thr Trp Asn Ala Xaa Lys Leu Thr Tyr Ile Asp Thr Lys Tyr Val Val
            125                 130                 135 cat gtg aag agt tta gag aca gaa gaa gag caa cag tat ctc acc tca     646
His Val Lys Ser Leu Glu Thr Glu Glu Glu Gln Gln Tyr Leu Thr Ser
        140                 145                 150 agc tat att aac atc tcc act gat tca tta caa ggt ggc aag aag tac     694
Ser Tyr Ile Asn Ile Ser Thr Asp Ser Leu Gln Gly Gly Lys Lys Tyr
155                 160                 165 ttg gtt tgg gtc caa gca gca aac gca cta ggc atg gaa gag tca aaa     742
```

```
Leu Val Trp Val Gln Ala Ala Asn Ala Leu Gly Met Glu Glu Ser Lys
170                 175                 180                 185 caa ctg caa att cac ctg gat gat ata gtg ata cct tct gca gcc gtc        790
Gln Leu Gln Ile His Leu Asp Asp Ile Val Ile Pro Ser Ala Ala Val
                    190                 195                 200 att tcc agg gct gag act ata aat gct aca gtg ccc aag acc ata att        838
Ile Ser Arg Ala Glu Thr Ile Asn Ala Thr Val Pro Lys Thr Ile Ile
                205                 210                 215 tat tgg gat agt caa aca aca att gaa aag gtt tcc tgt gaa atg aga        886
Tyr Trp Asp Ser Gln Thr Thr Ile Glu Lys Val Ser Cys Glu Met Arg
            220                 225                 230 tac aag gct aca aca aac caa act tgg aat gtt aaa gaa ttt gac acc        934
Tyr Lys Ala Thr Thr Asn Gln Thr Trp Asn Val Lys Glu Phe Asp Thr
235                 240                 245 aat ttt aca tat gtg caa cag tca gaa ttc tac ttg gag cca aac att        982
Asn Phe Thr Tyr Val Gln Gln Ser Glu Phe Tyr Leu Glu Pro Asn Ile
250                 255                 260                 265 aag tac gta ttt caa gtg aga tgt caa gaa aca ggc aaa agg tac tgg       1030
Lys Tyr Val Phe Gln Val Arg Cys Gln Glu Thr Gly Lys Arg Tyr Trp
                270                 275                 280 cag cct tgg agt tca ccg ttt ttt cat aaa aca cct gaa aca gtt ccc       1078
Gln Pro Trp Ser Ser Pro Phe Phe His Lys Thr Pro Glu Thr Val Pro
                285                 290                 295 cag gtc aca tca aaa gca ttc caa cat gac aca tgg aat tct ggg cta       1126
Gln Val Thr Ser Lys Ala Phe Gln His Asp Thr Trp Asn Ser Gly Leu
            300                 305                 310 aca gtt gct tcc atc tct aca ggg cac ctt act tct gac aac aga gga       1174
Thr Val Ala Ser Ile Ser Thr Gly His Leu Thr Ser Asp Asn Arg Gly
315                 320                 325 gac att gga ctt tta ttg gga atg atc gtc ttt gct gtt atg ttg tca       1222
Asp Ile Gly Leu Leu Leu Gly Met Ile Val Phe Ala Val Met Leu Ser
330                 335                 340                 345 att ctt tct ttg att ggg ata ttt aac aga tca ttc cga act ggg att       1270
Ile Leu Ser Leu Ile Gly Ile Phe Asn Arg Ser Phe Arg Thr Gly Ile
                350                 355                 360 aaa aga agg atc tta ttg tta ata cca aag tgg ctt tat gaa gat att       1318
Lys Arg Arg Ile Leu Leu Leu Ile Pro Lys Trp Leu Tyr Glu Asp Ile
                365                 370                 375 cct aat atg aaa aac agc aat gtt gtg aaa atg cta cag gaa aat agt       1366
Pro Asn Met Lys Asn Ser Asn Val Val Lys Met Leu Gln Glu Asn Ser
            380                 385                 390 gaa ctt atg aat aat aat tcc agt gag cag gtc cta tat gtt gat ccc       1414
Glu Leu Met Asn Asn Asn Ser Ser Glu Gln Val Leu Tyr Val Asp Pro
395                 400                 405 atg att aca gag ata aaa gaa atc ttc atc cca gaa cac aag cct aca       1462
Met Ile Thr Glu Ile Lys Glu Ile Phe Ile Pro Glu His Lys Pro Thr
410                 415                 420                 425 gac tac aag aag gag aat aca gga ccc ctg gag aca aga gac tac ccg       1510
Asp Tyr Lys Lys Glu Asn Thr Gly Pro Leu Glu Thr Arg Asp Tyr Pro
                430                 435                 440 caa aac tcg cta ttc gac aat act aca gtt gta tat att cct gat ctc       1558
Gln Asn Ser Leu Phe Asp Asn Thr Thr Val Val Tyr Ile Pro Asp Leu
                445                 450                 455 aac act gga tat aaa ccc caa att tca aat ttt ctg cct gag gga agc       1606
Asn Thr Gly Tyr Lys Pro Gln Ile Ser Asn Phe Leu Pro Glu Gly Ser
            460                 465                 470 cat ctc agc aat aat aat gaa att act tcc tta aca ctt aaa cca cca       1654
His Leu Ser Asn Asn Asn Glu Ile Thr Ser Leu Thr Leu Lys Pro Pro
475                 480                 485
```

-continued

```
gtt gat tcc tta gac tca gga aat aat ccc agg tta caa aag cat cct    1702
Val Asp Ser Leu Asp Ser Gly Asn Asn Pro Arg Leu Gln Lys His Pro
490                 495                 500                 505 aat ttt gct ttt tct gtt tca agt gtg aat tca cta agc aac aca ata    1750
Asn Phe Ala Phe Ser Val Ser Ser Val Asn Ser Leu Ser Asn Thr Ile
                510                 515                 520 ttt ctt gga gaa tta agc ctc ata tta aat caa gga gaa tgc agt tct    1798
Phe Leu Gly Glu Leu Ser Leu Ile Leu Asn Gln Gly Glu Cys Ser Ser
            525                 530                 535 cct gac ata caa aac tca gta gag gag gaa acc acc atg ctt ttg gaa    1846
Pro Asp Ile Gln Asn Ser Val Glu Glu Glu Thr Thr Met Leu Leu Glu
        540                 545                 550 aat gat tca ccc agt gaa act att cca gaa cag acc ctg ctt cct gat    1894
Asn Asp Ser Pro Ser Glu Thr Ile Pro Glu Gln Thr Leu Leu Pro Asp
    555                 560                 565 gaa ttt gtc tcc tgt ttg ggg atc gtg aat gag gag ttg cca tct att    1942
Glu Phe Val Ser Cys Leu Gly Ile Val Asn Glu Glu Leu Pro Ser Ile
570                 575                 580                 585 aat act tat ttt cca caa aat att ttg gaa agc cac ttc aat agg att    1990
Asn Thr Tyr Phe Pro Gln Asn Ile Leu Glu Ser His Phe Asn Arg Ile
                590                 595                 600 tca ctc ttg gaa aag tagagctgtg tggtcaaaat caatatgaga aagctgcctt   2045
Ser Leu Leu Glu Lys
            605 gcaatctgaa cttgggtttt ccctgcaata gaaattgaat tctgcctctt tttgaaaaaa   2105 atgtattcac atacaaatct tcacatggac acatgttttc atttcccttg gataaatacc   2165 taggtagggg attgctgggc catatgataa gcatatgttt cagttctacc aatcttgttt   2225 ccagagtagt gacatttctg tgctcctacc atcaccatgt aagaattccc gggagctcca   2285 tgccttttta attttagcca ttcttctgcc tmatttctta aaattagaga attaaggtcc   2345 cgaaggtgga acatgcttca tggtcacaca tacaggcaca aaaacagcat tatgtggacg   2405 cctcatgtat tttttataga gtcaactatt tcctctttat tttccctcat tgaaagatgc   2465 aaaacagctc tctattgtgt acagaaaggg taaataatgc aaaataccctg gtagtaaaat   2525 aaatgctgaa aattttcctt taaaatagaa tcattaggcc aggcgtggtg gctcatgctt   2585 gtaatcccag cactttggta ggctgaggtr ggtggatcac ctgaggtcag gagttcgagt   2645 ccagcctggc caatatgctg aaaccctgtc tctactaaaa ttacaaaaat tagccggcca   2705 tggtggcagg tgcttgtaat cccagctact gggaggctg aggcaggaga atcacttgaa   2765 ccaggaaggc agaggttgca ctgagctgag attgtgccac tgcactccag cctgggcaac   2825 aagagcaaaa ctctgtctgg aaaaaaaaaa aaaa                              2859
```

<210> SEQ ID NO 6
<211> LENGTH: 629
<212> TYPE: PRT
<213> ORGANISM: Homo sapiens
<220> FEATURE:
<221> NAME/KEY: misc_feature
<222> LOCATION: (-21)..(-21)
<223> OTHER INFORMATION: The 'Xaa' at location -21 stands for Gln, or His.
<220> FEATURE:
<221> NAME/KEY: misc_feature
<222> LOCATION: (126)..(126)
<223> OTHER INFORMATION: The 'Xaa' at location 126 stands for Gly, or Arg.

<400> SEQUENCE: 6

Met Asn Xaa Val Thr Ile Gln Trp Asp Ala Val Ile Ala Leu Tyr Ile

-continued

```
                    -20                  -15                  -10
Leu Phe Ser Trp Cys His Gly Gly Ile Thr Asn Ile Asn Cys Ser Gly
            -5               -1   1               5

His Ile Trp Val Glu Pro Ala Thr Ile Phe Lys Met Gly Met Asn Ile
 10                  15                  20                  25

Ser Ile Tyr Cys Gln Ala Ala Ile Lys Asn Cys Gln Pro Arg Lys Leu
                 30                  35                  40

His Phe Tyr Lys Asn Gly Ile Lys Glu Arg Phe Gln Ile Thr Arg Ile
             45                  50                  55

Asn Lys Thr Thr Ala Arg Leu Trp Tyr Lys Asn Phe Leu Glu Pro His
         60                  65                  70

Ala Ser Met Tyr Cys Thr Ala Glu Cys Pro Lys His Phe Gln Glu Thr
 75                  80                  85

Leu Ile Cys Gly Lys Asp Ile Ser Ser Gly Tyr Pro Pro Asp Ile Pro
 90                  95                 100                 105

Asp Glu Val Thr Cys Val Ile Tyr Glu Tyr Ser Gly Asn Met Thr Cys
                110                 115                 120

Thr Trp Asn Ala Xaa Lys Leu Thr Tyr Ile Asp Thr Lys Tyr Val Val
            125                 130                 135

His Val Lys Ser Leu Glu Thr Glu Glu Gln Gln Tyr Leu Thr Ser
        140                 145                 150

Ser Tyr Ile Asn Ile Ser Thr Asp Ser Leu Gln Gly Gly Lys Lys Tyr
        155                 160                 165

Leu Val Trp Val Gln Ala Ala Asn Ala Leu Gly Met Glu Glu Ser Lys
170                 175                 180                 185

Gln Leu Gln Ile His Leu Asp Asp Ile Val Ile Pro Ser Ala Ala Val
                190                 195                 200

Ile Ser Arg Ala Glu Thr Ile Asn Ala Thr Val Pro Lys Thr Ile Ile
            205                 210                 215

Tyr Trp Asp Ser Gln Thr Thr Ile Glu Lys Val Ser Cys Glu Met Arg
            220                 225                 230

Tyr Lys Ala Thr Thr Asn Gln Thr Trp Asn Val Lys Glu Phe Asp Thr
235                 240                 245

Asn Phe Thr Tyr Val Gln Gln Ser Glu Phe Tyr Leu Glu Pro Asn Ile
250                 255                 260                 265

Lys Tyr Val Phe Gln Val Arg Cys Gln Glu Thr Gly Lys Arg Tyr Trp
                270                 275                 280

Gln Pro Trp Ser Ser Pro Phe Phe His Lys Thr Pro Glu Thr Val Pro
            285                 290                 295

Gln Val Thr Ser Lys Ala Phe Gln His Asp Thr Trp Asn Ser Gly Leu
            300                 305                 310

Thr Val Ala Ser Ile Ser Thr Gly His Leu Thr Ser Asp Asn Arg Gly
315                 320                 325

Asp Ile Gly Leu Leu Leu Gly Met Ile Val Phe Ala Val Met Leu Ser
330                 335                 340                 345

Ile Leu Ser Leu Ile Gly Ile Phe Asn Arg Ser Phe Arg Thr Gly Ile
                350                 355                 360

Lys Arg Arg Ile Leu Leu Leu Ile Pro Lys Trp Leu Tyr Glu Asp Ile
            365                 370                 375

Pro Asn Met Lys Asn Ser Asn Val Val Lys Met Leu Gln Glu Asn Ser
        380                 385                 390

Glu Leu Met Asn Asn Asn Ser Ser Glu Gln Val Leu Tyr Val Asp Pro
    395                 400                 405
```

-continued

Met Ile Thr Glu Ile Lys Glu Ile Phe Ile Pro Glu His Lys Pro Thr
410                 415                 420                 425

Asp Tyr Lys Lys Glu Asn Thr Gly Pro Leu Glu Thr Arg Asp Tyr Pro
            430                 435                 440

Gln Asn Ser Leu Phe Asp Asn Thr Val Val Tyr Ile Pro Asp Leu
        445                 450                 455

Asn Thr Gly Tyr Lys Pro Gln Ile Ser Asn Phe Leu Pro Glu Gly Ser
            460                 465                 470

His Leu Ser Asn Asn Glu Ile Thr Ser Leu Thr Leu Lys Pro Pro
475                 480                 485

Val Asp Ser Leu Asp Ser Gly Asn Asn Pro Arg Leu Gln Lys His Pro
490                 495                 500                 505

Asn Phe Ala Phe Ser Val Ser Val Asn Ser Leu Ser Asn Thr Ile
                510                 515                 520

Phe Leu Gly Glu Leu Ser Leu Ile Leu Asn Gln Gly Glu Cys Ser Ser
            525                 530                 535

Pro Asp Ile Gln Asn Ser Val Glu Glu Thr Thr Met Leu Leu Glu
        540                 545                 550

Asn Asp Ser Pro Ser Glu Thr Ile Pro Glu Gln Thr Leu Leu Pro Asp
555                 560                 565

Glu Phe Val Ser Cys Leu Gly Ile Val Asn Glu Glu Leu Pro Ser Ile
570                 575                 580                 585

Asn Thr Tyr Phe Pro Gln Asn Ile Leu Glu Ser His Phe Asn Arg Ile
            590                 595                 600

Ser Leu Leu Glu Lys
            605

<210> SEQ ID NO 7
<211> LENGTH: 862
<212> TYPE: PRT
<213> ORGANISM: Homo sapiens

<400> SEQUENCE: 7

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile

-continued

```
                165                 170                 175
Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
            195                 200                 205

Ser Ser Ser Leu Pro Ser Thr Phe Thr Phe Leu Asp Ile Val Arg Pro
            210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
            275                 280                 285

Glu Tyr Glu Phe Gln Ile Ser Ser Lys Leu His Leu Tyr Lys Gly Ser
            290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
            355                 360                 365

Gly Gly Lys Ala Met Thr Gln Asn Ile Thr Gly His Thr Ser Trp Thr
370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
            435                 440                 445

Ser Ala Val Gln Glu Tyr Val Val Glu Trp Arg Glu Leu His Pro Gly
450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
            515                 520                 525

Ala Ile Thr Glu Glu Lys Gly Ser Ile Leu Ile Ser Trp Asn Ser Ile
            530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590
```

```
Thr Tyr Val Leu Trp Met Thr Ala Leu Thr Ala Ala Gly Glu Ser Ser
            595                 600                 605

His Gly Asn Glu Arg Glu Phe Cys Leu Gln Gly Lys Ala Asn Trp Met
    610                 615                 620

Ala Phe Val Ala Pro Ser Ile Cys Ile Ala Ile Met Val Gly Ile
625                 630                 635                 640

Phe Ser Thr His Tyr Phe Gln Gln Lys Val Phe Val Leu Leu Ala Ala
                645                 650                 655

Leu Arg Pro Gln Trp Cys Ser Arg Glu Ile Pro Asp Pro Ala Asn Ser
            660                 665                 670

Thr Cys Ala Lys Lys Tyr Pro Ile Ala Glu Glu Lys Thr Gln Leu Pro
        675                 680                 685

Leu Asp Arg Leu Ile Asp Trp Pro Thr Pro Glu Asp Pro Glu Pro
690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
                725                 730                 735

Gln Ala Ser Glu Lys Asp Met Met His Ser Ala Ser Ser Pro Pro
            740                 745                 750

Pro Arg Ala Leu Gln Ala Glu Ser Arg Gln Leu Val Asp Leu Tyr Lys
        755                 760                 765

Val Leu Glu Ser Arg Gly Ser Asp Pro Lys Pro Glu Asn Pro Ala Cys
770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
                805                 810                 815

Asp Ser Leu Glu Glu Leu Glu Pro Gln His Ile Ser Leu Ser Val Phe
            820                 825                 830

Pro Ser Ser Ser Leu His Pro Leu Thr Phe Ser Cys Gly Asp Lys Leu
        835                 840                 845

Thr Leu Asp Gln Leu Lys Met Arg Cys Asp Ser Leu Met Leu
        850                 855                 860

<210> SEQ ID NO 8
<211> LENGTH: 328
<212> TYPE: PRT
<213> ORGANISM: Homo sapiens

<400> SEQUENCE: 8

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
```

-continued

```
                100                 105                 110
Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 9
<211> LENGTH: 335
<212> TYPE: PRT
<213> ORGANISM: Mus musculus

<400> SEQUENCE: 9

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140
```

```
Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
            165                 170                 175

Val Thr Leu Asp Gln Arg Asp Tyr Glu Lys Tyr Ser Val Ser Cys Gln
        180                 185                 190

Glu Asp Val Thr Cys Pro Thr Ala Glu Glu Thr Leu Pro Ile Glu Leu
    195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
            245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 10
<211> LENGTH: 531
<212> TYPE: PRT
<213> ORGANISM: Mus musculus

<400> SEQUENCE: 10

Met Ser Ala Leu Leu Ile Leu Ala Leu Val Gly Ala Ala Val Ala Asp
1               5                   10                  15

Tyr Lys Asp Asp Asp Asp Lys Leu Met Trp Glu Leu Glu Lys Asp Val
            20                  25                  30

Tyr Val Val Glu Val Asp Trp Thr Pro Asp Ala Pro Gly Glu Thr Val
        35                  40                  45

Asn Leu Thr Cys Asp Thr Pro Glu Glu Asp Asp Ile Thr Trp Thr Ser
    50                  55                  60

Asp Gln Arg His Gly Val Ile Gly Ser Gly Lys Thr Leu Thr Ile Thr
65                  70                  75                  80

Val Lys Glu Phe Leu Asp Ala Gly Gln Tyr Thr Cys His Lys Gly Gly
                85                  90                  95

Glu Thr Leu Ser His Ser His Leu Leu Leu His Lys Lys Glu Asn Gly
            100                 105                 110

Ile Trp Ser Thr Glu Ile Leu Lys Asn Phe Lys Asn Lys Thr Phe Leu
        115                 120                 125

Lys Cys Glu Ala Pro Asn Tyr Ser Gly Arg Phe Thr Cys Ser Trp Leu
    130                 135                 140

Val Gln Arg Asn Met Asp Leu Lys Phe Asn Ile Lys Ser Ser Ser Ser
145                 150                 155                 160

Ser Pro Asp Ser Arg Ala Val Thr Cys Gly Met Ala Ser Leu Ser Ala
                165                 170                 175

Glu Lys Val Thr Leu Asp Gln Arg Asp Tyr Glu Lys Tyr Ser Val Ser
            180                 185                 190
```

```
Cys Gln Glu Asp Val Thr Cys Pro Thr Ala Glu Glu Thr Leu Pro Ile
        195                 200                 205

Glu Leu Ala Leu Glu Ala Arg Gln Gln Asn Lys Tyr Glu Asn Tyr Ser
    210                 215                 220

Thr Ser Phe Phe Ile Arg Asp Ile Ile Lys Pro Asp Pro Pro Lys Asn
225                 230                 235                 240

Leu Gln Met Lys Pro Leu Lys Asn Ser Gln Val Glu Val Ser Trp Glu
                245                 250                 255

Tyr Pro Asp Ser Trp Ser Thr Pro His Ser Tyr Phe Ser Leu Lys Phe
            260                 265                 270

Phe Val Arg Ile Gln Arg Lys Lys Glu Lys Met Lys Glu Thr Glu Glu
        275                 280                 285

Gly Cys Asn Gln Lys Gly Ala Phe Leu Val Glu Lys Thr Ser Thr Glu
    290                 295                 300

Val Gln Cys Lys Gly Gly Asn Val Cys Val Gln Ala Gln Asp Arg Tyr
305                 310                 315                 320

Tyr Asn Ser Ser Cys Ser Lys Trp Ala Cys Val Pro Cys Arg Val Arg
                325                 330                 335

Ser Ser Arg Gly Gly Ser Gly Ser Gly Gly Gly Ser
            340                 345                 350

Lys Leu Leu Ala Val Pro Arg Ser Ser Pro Asp Trp Ala Gln Cys
        355                 360                 365

Gln Gln Leu Ser Arg Asn Leu Cys Met Leu Ala Trp Asn Ala His Ala
    370                 375                 380

Pro Ala Gly His Met Asn Leu Leu Arg Glu Glu Asp Glu Thr
385                 390                 395                 400

Lys Asn Asn Val Pro Arg Ile Gln Cys Glu Asp Gly Cys Asp Pro Gln
                405                 410                 415

Gly Leu Lys Asp Asn Ser Gln Phe Cys Leu Gln Arg Ile Arg Gln Gly
            420                 425                 430

Leu Val Phe Tyr Lys His Leu Leu Asp Ser Asp Ile Phe Lys Gly Glu
        435                 440                 445

Pro Ala Leu Leu Pro Asp Ser Pro Met Glu Gln Leu His Thr Ser Leu
450                 455                 460

Leu Gly Leu Ser Gln Leu Leu Gln Pro Glu Asp His Pro Arg Glu Thr
465                 470                 475                 480

Gln Gln Met Pro Ser Leu Ser Ser Ser Gln Gln Trp Gln Arg Pro Leu
                485                 490                 495

Leu Arg Ser Lys Ile Leu Arg Ser Leu Gln Ala Phe Leu Ala Ile Ala
            500                 505                 510

Ala Arg Val Phe Ala His Gly Ala Ala Thr Leu Thr Glu Pro Leu Val
        515                 520                 525

Pro Thr Ala
    530

<210> SEQ ID NO 11
<211> LENGTH: 521
<212> TYPE: PRT
<213> ORGANISM: Homo sapiens

<400> SEQUENCE: 11

Met Ser Ala Leu Leu Ile Leu Ala Leu Val Gly Ala Ala Val Ala Asp
1               5                   10                  15

Tyr Lys Asp Asp Asp Asp Lys Leu Ile Trp Glu Leu Lys Lys Asp Val
```

-continued

```
                20                  25                  30
Tyr Val Val Glu Leu Asp Trp Tyr Pro Asp Ala Pro Gly Glu Met Val
             35                  40                  45
Val Leu Thr Cys Asp Thr Pro Glu Glu Asp Gly Ile Thr Trp Thr Leu
 50                  55                  60
Asp Gln Ser Ser Glu Val Leu Gly Ser Gly Lys Thr Leu Thr Ile Gln
 65                  70                  75                  80
Val Lys Glu Phe Gly Asp Ala Gly Gln Tyr Thr Cys His Lys Gly Gly
                 85                  90                  95
Glu Val Leu Ser His Ser Leu Leu Leu Leu His Lys Lys Glu Asp Gly
                100                 105                 110
Ile Trp Ser Thr Asp Ile Leu Lys Asp Gln Lys Glu Pro Lys Asn Lys
             115                 120                 125
Thr Phe Leu Arg Cys Glu Ala Lys Asn Tyr Ser Gly Arg Phe Thr Cys
 130                 135                 140
Trp Trp Leu Thr Thr Ile Ser Thr Asp Leu Thr Phe Ser Val Lys Ser
 145                 150                 155                 160
Ser Arg Gly Ser Ser Asp Pro Gln Gly Val Thr Cys Gly Ala Ala Thr
                165                 170                 175
Leu Ser Ala Glu Arg Val Arg Gly Asp Asn Lys Glu Tyr Glu Tyr Ser
             180                 185                 190
Val Glu Cys Gln Glu Asp Ser Ala Cys Pro Ala Ala Glu Glu Ser Leu
             195                 200                 205
Pro Ile Glu Val Met Val Asp Ala Val His Lys Leu Lys Tyr Glu Asn
 210                 215                 220
Tyr Thr Ser Ser Phe Phe Ile Arg Asp Ile Ile Lys Pro Asp Pro Pro
 225                 230                 235                 240
Asn Asn Leu Gln Leu Lys Pro Leu Lys Asn Ser Arg Gln Val Glu Val
                245                 250                 255
Ser Trp Glu Tyr Pro Asp Thr Trp Ser Thr Pro His Ser Tyr Phe Ser
             260                 265                 270
Leu Thr Phe Cys Val Gln Val Gln Gly Lys Ser Lys Arg Glu Lys Lys
             275                 280                 285
Asp Arg Val Phe Thr Asp Lys Thr Ser Ala Thr Val Ile Cys Arg Lys
 290                 295                 300
Asn Ala Ser Ile Ser Val Arg Ala Gln Asp Arg Tyr Tyr Ser Ser Ser
 305                 310                 315                 320
Trp Ser Glu Trp Ala Ser Val Pro Cys Ser Gly Ser Gly Ser Ser Arg
                325                 330                 335
Gly Gly Ser Gly Ser Gly Gly Ser Gly Gly Gly Ser Lys Leu Arg
             340                 345                 350
Ala Val Pro Gly Gly Ser Ser Pro Ala Trp Thr Gln Cys Gln Gln Leu
             355                 360                 365
Ser Gln Lys Leu Cys Thr Leu Ala Trp Ser Ala His Pro Leu Val Gly
             370                 375                 380
His Met Asp Leu Arg Glu Glu Gly Asp Glu Glu Thr Thr Asn Asp Val
 385                 390                 395                 400
Pro His Ile Gln Cys Gly Asp Gly Cys Asp Pro Gln Gly Leu Arg Asp
                405                 410                 415
Asn Ser Gln Phe Cys Leu Gln Arg Ile His Gln Gly Leu Ile Phe Tyr
             420                 425                 430
Glu Lys Leu Leu Gly Ser Asp Ile Phe Thr Gly Glu Pro Ser Leu Leu
             435                 440                 445
```

```
-continued

Pro Asp Ser Pro Val Ala Gln Leu His Ala Ser Leu Leu Gly Leu Ser
    450                 455                 460

Gln Leu Leu Gln Pro Glu Gly His His Trp Glu Thr Gln Gln Ile Pro
465                 470                 475                 480

Ser Leu Ser Pro Ser Gln Pro Trp Gln Arg Leu Leu Leu Arg Phe Lys
                485                 490                 495

Ile Leu Arg Ser Leu Gln Ala Phe Val Ala Val Ala Ala Arg Val Phe
            500                 505                 510

Ala His Gly Ala Ala Thr Leu Ser Pro
        515                 520
```

USES OF IL-23 AGONISTS AND ANTAGONISTS; RELATED REAGENTS

This application claims benefit from U.S. Provisional Patent Application No. 60/453,672, filed Mar. 10, 2003.

FIELD OF THE INVENTION

The present invention concerns uses of mammalian cytokine molecules and related reagents. More specifically, the invention relates to identification of mammalian cytokine-like proteins and inhibitors thereof that can be used in the treatment of proliferative disorders.

BACKGROUND OF THE INVENTION

Cancers and tumors can be controlled or eradicated by the immune system. The immune system includes several types of lymphoid and myeloid cells, e.g., monocytes, macrophages, dendritic cells (DCs), eosinophils, T cells, B cells, and neutrophils. These lymphoid and myeloid cells produce secreted signaling proteins known as cytokines. The cytokines include, e.g., interleukin-10 (IL-10), interferon-gamma (IFNgamma), IL-12, and IL-23. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders, whereas impaired immune response may result in cancer. Anti-tumor response by the immune system includes innate immunity, e.g., as mediated by macrophages, NK cells, and neutrophils, and adaptive immunity, e.g., as mediated by antigen presenting cells (APCs), T cells, and B cells (see, e.g., Abbas, et al. (eds.) (2000) *Cellular and Molecular Immunology*, W. B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Methods of modulating immune response have been used in the treatment of cancers, e.g., melanoma. These methods include treatment with cytokines or anti-cytokine antibodies, such as IL-2, IL-12, tumor necrosis factor-alpha (TNFalpha), IFNgamma, granulocyte macrophage-colony stimulating factor (GM-CSF), and transforming growth factor (TGF). Where a cancer cell can produces a cytokine that enhance its own growth or its own survival, an anti-cytokine antibody may be an appropriate therapeutic agent (see, e.g., Ramirez-Montagut, et al. (2003) *Oncogene* 22:3180-3187; Braun, et al. (2000) *J. Immunol.* 164:4025-4031; Shaw, et al. (1998) *J. Immunol.* 161:2817-2824; Coussens and Werb (2002) *Nature* 420:860-867; Baxevanis, et al. (2000) *J. Immunol.* 164:3902-3912; Shimizu, et al. (1999) *J. Immunol.* 163:5211-5218; Belardelli and Ferrantini (2002) *TRENDS Immunol.* 23:201-208; Seki, et al. (2002) *J. Immunol.* 168:3484-3492; Casares, et al. (2003) *J. Immunol.* 171:5931-5939; Oft, et al. (2002) *Nature Cell Biol.* 4:487-494)

Interleukin-23 (IL-23) is a heterodimeric cytokine comprised of two subunits, i.e., p19 and p40. The p19 subunit is structurally related to IL-6, granulocyte-colony stimulating factor (G-CSF), and the p35 subunit of IL-12. The p40 subunit of IL-23 is also part of IL-12, a heterodimeric cytokine comprising p35 and p40. IL-23 mediates signaling by binding to a heterodimeric receptor, comprised of IL-23R and IL-12beta1. The IL-12beta1 subunit is shared by the IL-12 receptor, which is composed of IL-12beta1 and IL-12beta2. A number of early studies demonstrated that the physiological consequences of a genetic deficiency in p40 (p40 knockout mouse; p40KO mouse; $p40^{-/-}$ mouse) were different from, e.g., more severe or less severe, than those found in a p35KO mouse. Some of these results were eventually explained by the discovery of IL-23, and the finding that the p40KO prevents expression of both IL-12 and IL-23 (Oppmann, et al. (2000) *Immunity* 13:715-725; Wiekowski, et al. (2001) *J. Immunol.* 166:7563-7570; Parham, et al.(2002). *J Immunol* 168, 5699-708; Frucht (2002) *Sci STKE* 2002, E1-E3; Elkins, et al. (2002) *Infection Immunity* 70:1936-1948; Cua, et al. (2003) *Nature* 421:744-748).

Present methods for treating cancer are not completely effective, and cytokines, such as IL-12 or IFNgamma produce toxic side effects (see, e.g., Naylor and Hadden (2003) *Int. Immunopharmacol.* 3:1205-1215; Fernandez, et al. (1999) *J. Immunol.* 162:609-617). The present invention addresses these problems by providing methods of using agonists and antagonists of IL-23.

SUMMARY OF THE INVENTION

The present invention is based upon the discovery that an agonist or antagonist of IL-23 can modulate tumor growth.

The present invention provides a method of modulating tumor growth comprising contacting a tumor cell with an effective amount of an agonist or antagonist of IL-23. Also provided is the above method, wherein the antagonist of IL-23 inhibits or prevents tumor growth; as well as the above method wherein the tumor cell expresses IL-23. In another aspect, the present invention provides the above method wherein the agonist or antagonist of IL-23 comprises a binding composition that specifically binds a polypeptide or nucleic acid of p19 (SEQ ID NOs:1, 2, 3, or 4); or IL-23R (SEQ ID NOs:5 or 6); or the above method wherein the binding composition comprises: an antigen-binding site of an antibody; an extracellular region of IL-23R (SEQ ID NOs:5 or 6); a small molecule; an anti-sense nucleic acid or small interference RNA (siRNA); or a detectable label; and the above method wherein the binding composition comprises: a polyclonal antibody; a monoclonal antibody; a humanized antibody, or a fragment thereof; an Fab, Fv, or $F(ab')_2$ fragment; or a peptide mimetic of an antibody.

Yet another embodiment of the present invention provides a method of modulating tumor growth comprising contacting a tumor cell with an effective amount of an agonist or antagonist of IL-23; wherein the tumor cell is: a colon cancer cell; an ovarian cancer cell; a breast cancer cell; or a melanoma cell.

In another aspect, the invention provides a method of treating a subject suffering from a cancer or tumor comprising administering to the subject an effective amount of an agonist or antagonist of IL-23; and the above method wherein the antagonist of IL-23 inhibits: growth of the cancer or tumor; cachexia; anorexia; or angiogenesis. Also provided is the above method wherein the antagonist of IL-23 comprises a binding composition that specifically binds a polypeptide or nucleic acid of: p19 (SEQ ID NOs:1, 2, 3, or 4) or IL-23R (SEQ ID NOs:5 or 6). Yet another embodiment of the present invention provides the above method wherein the binding composition comprises: an antigen-binding site of an antibody; an extracellular region of IL-23R (SEQ ID NOs:5 or 6); an anti-sense nucleic acid or small interference RNA (siRNA); a small molecule; or a detectable label; and the above method wherein the binding composition comprises: a polyclonal antibody; a monoclonal antibody; a humanized antibody, or a fragment thereof; an Fab, Fv, or F(ab')$_2$ fragment; or a peptide mimetic of an antibody.

In another embodiment, the invention provides the above method wherein the cancer or tumor is of the: gastrointestinal tract; respiratory tract; reproductive system; or endocrine system; as well as the above method wherein the cancer or tumor is: colon cancer; ovarian cancer; a melanoma; or breast cancer.

In other aspect of the present invention provides a method of diagnosis of a cancer or tumor comprising contacting a sample from a subject with the binding compositions of the above method, as well as the above method of diagnosis, wherein the binding composition comprises a nucleic acid probe or primer that specifically binds or hybridizes to the polynucleotide of SEQ ID NOs:1, 2, or 5.

Yet another embodiment of the present invention provides a kit for the diagnosis of a cancer or tumor comprising the binding composition of the above method and a compartment or instructions for use or disposal. Also provided is the above kit wherein the binding composition comprises an antibody that specifically binds to p19 (SEQ ID NOs:1, 2, 3, or 4) or IL-23R (SEQ ID NOs:5 or 6).

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. Definitions.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an IL-23 agonist or IL-23 antagonist to a human or animal subject, a cell, tissue, physiological compartment, or physiological fluid. "Treatment of a cell" also encompasses situations where the IL-23 agonist or IL-23 antagonist contacts IL-23 receptor (heterodimer of IL-23R and IL-12Rbeta1), e.g., in the fluid phase or colloidal phase, as well as situations where the agonist or antagonist contacts a fluid, e.g., where the fluid is in contact with a cell or receptor, but where it has not been demonstrated that the agonist or antagonist contacts the cell or receptor.

"Binding composition" refers to a molecule, small molecule, macromolecule, antibody, a fragment or analogue thereof, or soluble receptor, capable of binding to a target. "Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive. "Binding" may be defined as an association of the binding composition with a target where the association results in reduction in the normal Brownian motion of the binding composition, in cases where the binding composition can be dissolved or suspended in solution.

"Cachexia" is a wasting syndrome involving loss of muscle (muscle wasting) and fat, resulting from a disorder in metabolism. Cachexia occurs in various cancers, chronic pulmonary obstructive disorder (COPD), advanced organ failure, and AIDS. "Cancer cachexia" is the cachexia that occurs with cancer. Cancer cachexia is characterized by, e.g., marked weight loss, anorexia, asthenia, and anemia. Anorexia is a disorder resulting from lack of motivation to eat, e.g., food aversion (see, e.g., MacDonald, et al. (2003) *J. Am. Coll. Surg.* 197:143-161; Rubin (2003) *Proc. Natl. Acad. Sci. USA* 100:5384-5389; Tisdale (2002) *Nature Reviews Cancer* 2:862-871; Argiles, et al. (2003) *Drug Discovery Today* 8:838-844; Lelli, et al. (2003) *J. Chemother.* 15:220-225; Argiles, et al. (2003) *Curr. Opin. Clin. Nutr. Metab. Care* 6:401-406).

"Conservatively modified variants" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist irradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Inhibitors" and "antagonists" or "activators" and "agonists" refer to inhibitory or activating molecules, respectively, e.g., for the activation of, e.g., a ligand, receptor, cofactor, gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, fluorescent dyes, electron-dense reagents, substrates, epitope tags, or enzymes, e.g., as used in enzyme-linked immunoassays, or fluorettes (see, e.g., Rozinov and Nolan (1998) *Chem. Biol.* 5:713-728).

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor without significantly influencing its biological properties, e.g., signaling or adhesion. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antibody, or binding composition derived thereof. In a preferred embodiment the antibody will have an affinity that is greater than about $10^9$ liters/mol, as determined, e.g., by Scatchard analysis (Munsen, et al. (1980) *Analyt. Biochem.* 107:220-239).

II. General.

The present invention provides methods of using polypeptides, nucleic acids, variants, muteins, and mimetics of the IL-23 heterodimer, p19 subunit, p40 subunit, the IL-23 receptor heterodimer, IL-23R subunit, or IL-12Rbeta1 subunit. Also provided are methods for using a hyperkine, i.e., a fusion protein comprising, e.g., the p19 subunit linked to the p40 subunit, as well as nucleic acids encoding the hyperkine (see, e.g., SEQ ID NOs:10 or 11) (Oppmann, et al., supra; Fischer, et al. (1997) *Nature Biotechnol.* 15:142-145; Rakemann, et al. (1999) *J. Biol. Chem.* 274:1257-1266; and Peters, et al.(1998) *J. Immunol.* 161:3575-3581).

Interleukin-23 (IL-23; a.k.a. IL-B30) is a heterodimeric cytokine composed of a novel p19 subunit (SEQ ID NOs: 2 or 4) and the p40 subunit (SEQ ID NOs: 8 or 9) of IL-12 (Oppmann, et al, supra). Like p35, p19 requires co-expression of p40 for biological activity (Wiekowski, et al., supra). The IL-23 receptor comprises a novel receptor subunit (IL-23R; SEQ ID NO: 6) that binds p19 and IL-12Rbeta1 (SEQ ID NO: 7) that binds p40 (see, e,g., Parham, et al. (2002) *J. Immunol.* 168:5699-5708). These two receptor subunits form the functional signaling complex and are expressed on $CD4^+CD45Rb^{lo}$ memory T cells as well as IFNgamma activated bone marrow macrophages (Parham, et al., supra).

Antibodies can be raised to various cytokine proteins, including individual, polymorphic, allelic, strain, or species variants, and fragments thereof, both in their naturally occurring (full-length) forms or in their recombinant forms (see, e.g., SEQ ID NO: 2, 4, 10, or 11). Additionally, antibodies can be raised to receptor proteins (see, e.g., SEQ ID NO: 6) in both their native (or active) forms or in their inactive, e.g., denatured, forms. Anti-idiotypic antibodies may also be used.

Administration of an IL-23 agonist, i.e., IL-23 or IL-23 hyperkine, can induce, e.g., proliferation of memory T cells, PHA blasts, CD45RO T cells, CD45RO T cells; enhance production of interferon-gamma (IFNgamma) by PHA blasts or CD45RO T cells. In contrast to IL-12, IL-23 preferentially stimulates memory as opposed to naïve T cell populations in both human and mouse. IL-23 activates a number of intracellular cell-signaling molecules, e.g., Jak2, Tyk2, Stat1, Stat2, Stat3, and Stat4. IL-12 activates this same group of molecules, but Stat4 response to IL-23 is relatively weak, while Stat4 response to IL-12 is strong (Oppmann, et al., supra; Parham, et al. (2002) *J. Immunol.* 168:5699-5708).

IL-12 and IL-23 engage similar signal transduction mechanisms. IL-23 engaging its receptor complex, activates Jak2, Tyk2, and Stat-1, -3, -4, and -5, as does IL-12.

However Stat-4 activation is significantly weaker in response to IL-23 than IL-12. Also, in contrast to IL-12, the most prominent Stat induced by IL-23 is Stat-3 (see, e.g., Parham, et al., supra).

Administration of the p19 subunit of IL-23 can result in, e.g., stunted growth, infertility, and death of animals, as well as inflammatory infiltrates, e.g., in the gastrointestinal tract, lungs, skin, and liver, and epithelial cell hyperplasia, microcytic anemia, increased neutrophil count, increased serum TNFalpha; and increased expression of acute phase genes in liver; (Wiekowski, et al., supra). Enhanced IL-23 expression occured in immortalized not transformed epithelial cell lines. Thus, IL-23 may provide an early signal of tumor potential in vivo.

Other studies have demonstrated that IL-23 modulates immune response to infection (see, e.g., Pirhonen, et al. (2002) *J. Immunol.* 169:5673-5678; Broberg, et al. (2002) *J. Interferon Cytokine Res.* 22:641-651; Elkins, et al. (2002) *Infection Immunity* 70:1936-1948; Cooper, et al. (2002) *J. Immunol.* 168:1322-1327).

With respect to cancer, the presence of a relatively high amount of transcript in biopsied tissue from an individual indicates a predisposition for the development of the disease, or can provide a means for detecting the disease prior to the appearance of actual clinical symptoms. Gene expression data is useful tool in the diagnosis and treatment of diseases and pathological conditions (see, e.g., Li and Wong (2001) *Genome Informatics* 12:3-13; Lockhart, et al. (1996) *Nature Biotechnol.* 14:1675-1680; Homey, et al. (2000) *J. Immunol.* 164:3465-3470; Debets, et al. (2000) *J. Immunol.* 165:4950-4956).

III. Agonists, Antagonists, and Binding Compositions.

The present invention provides methods of using agonists and antagonist of IL-23. An agonist of IL-23 encompasses, e.g., IL-23, an IL-23 variant, mutein, hyperkine, or peptide mimetic, agonistic antibodies to IL-23R, and nucleic acids encoding these agonists. Antagonists of IL-23 include, e.g., antibodies to IL-23, blocking antibodies to IL-23R, a soluble receptor based on the extracellular region of a subunit of the IL-23R, peptide mimetics thereto, and nucleic acids encoding these antagonists.

The present invention provides methods of using agonists and antagonists of p19, the complex of p19 and p40, IL-23R, and the complex of IL-23R and IL-12Rbeta1, including binding compositions that specifically bind to proteins and protein complexes of p19, the complex of p19 and p40, IL-23R, and the complex of IL-23R and IL-12Rbeta1.

An IL-23 hyperkine encompasses, e.g., a fusion protein comprising the polypeptide sequence of p19 and p40, where p19 and p40 occur in one continous polypeptide chain. The sequences of p19 and p40 may be in either order. The fusion protein may contain a linker sequence, residing in between the sequences of p19 and p40, in one continuous polypeptide chain.

Regions of increased antigenicity can be used for antibody generation. Regions of increased antigenicity of human p19 occur, e.g., at amino acids 16-28; 57-87; 110-114; 136-154; and 182-186 of GenBank AAQ89442 (gi: 37183284). Regions of increased antigenicity of human IL-23R occur, e.g., at amino acids 22-33; 57-63; 68-74; 101-112; 117-133; 164-177; 244-264; 294-302; 315-326; 347-354; 444-473; 510-530; and 554-558 of GenBank AAM44229 (gi: 21239252). Analysis was by a Parker plot using Vector NTI® Suite (Informax, Inc, Bethesda, Md.). The present invention also provides an IL-23 antagonist that is a soluble receptor, i.e., comprising an extracellular region of IL-23R, e.g., amino acids 1-353 of GenBankAAM44229, or a fragment thereof, where the extracellular region or fragment thereof specifically binds to IL-23. Mouse IL-23R is GenBank NP_653131 (gi:21362353). Muteins and variants are contemplated, e.g., pegylation or mutagenesis to remove or replace deamidating Asn residues.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998)*J. Immunol.* 160:1029; Tang, et al. (1999)*J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; U.S. Pat. No. 6,329,511 issued to Vasquez, et al.).

Purification of antigen is not necessary for the generation of antibodies. Immunization can be performed by DNA vector immunization, see, e.g., Wang, et al. (1997) *Virology* 228:278-284. Alternatively, animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7:283-290; Wright, et al. (2000) *Immunity* 13:233-242; Preston, et al. (1997) *Eur. J. Immunol.* 27:1911-1918). Resultant hybridomas can be screened for production of the desired antibody by functional assays or biological assays, that is, assays not dependent on possession of the purified antigen. Immunization with cells may prove superior for antibody generation than immunization with purified antigen (Kaithamana, et al. (1999) *J. Immunol.* 163:5157-5164).

Antibody to antigen and ligand to receptor binding properties can be measured, e.g., by surface plasmon resonance (Karlsson, et al. (1991) *J. Immunol. Methods* 145:229-240; Neri, et al. (1997) *Nat. Biotechnol.* 15:1271-1275; Jonsson, et al. (1991) *Biotechniques* 11:620-627) or by competition ELISA (Friguet, et al. (1985) *J. Immunol. Methods* 77:305-319; Hubble (1997) *Immunol. Today* 18:305-306). Antibodies can be used for affinity purification to isolate the antibody's target antigen and associated bound proteins, see, e.g., Wilchek, et al. (1984) *Meth. Enzymol.* 104:3-55.

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res.* (Suppl.) 9:3982s-3990s).

Soluble receptors comprising the extracellular domains of IL-23R or IL-12Rbeta1 receptor polypeptides are provided. Soluble receptors can be prepared and used according to standard methods (see, e.g., Jones, et al. (2002) *Biochim. Biophys. Acta* 1592:251-263; Prudhomme, et al. (2001) *Expert Opinion Biol. Ther.* 1:359-373; Fernandez-Botran (1999) *Crit. Rev. Clin. Lab Sci.* 36:165-224).

IV. Therapeutic Compositions, Methods.

The present invention provides IL-23 and anti-IL-23R for use, e.g., in the treatment of proliferative conditions and disorders, including cancer, tumors, angiogenesis, cachexia, cancer cachexia, anorexia, and pre-cancerous disorders, e.g., dysplasia. Nucleic acids are also provided for these therapeutic uses, e.g., nucleic acids encoding IL-23 or IL-23R, or an antigenic fragment thereof, the corresponding anti-sense nucleic acids, and hybridization products thereof. The invention also provides compositions for siRNA interference (see, e.g., Arenz and Schepers (2003) *Naturwissenschaften* 90:345-359; Sazani and Kole (2003) *J. Clin. Invest.* 112: 481-486; Pirollo, et al. (2003) *Pharmacol. Therapeutics* 99:55-77; Wang, et al. (2003) *Antisense Nucl. Acid Drug Devel.* 13:169-189).

To prepare pharmaceutical or sterile compositions including an agonist or antagonist of IL-23, the cytokine analogue or mutein, antibody thereto, or nucleic acid thereof, is admixed with a pharmaceutically acceptable carrier or excipient, see, e.g., *Remington's Pharmaceutical Sciences* and *U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, N.Y.; Lieberman, et al. (eds.) (1990) *Pharmaceutical Dosage Forms: Tablets*, Marcel Dekker, N.Y.; Lieberman, et al. (eds.) (1990) *Pharmaceutical Dosage Forms: Disperse Systems*, Marcel Dekker, N.Y.; Weiner and Kotkoskie (2000) *Excipient Toxicity and Safety*, Marcel Dekker, Inc., New York, N.Y.).

The route of administration is by, e.g., topical or cutaneous application, subcutaneous injection, injection or infusion by intravenous, intraperitoneal, intracerebral, intramuscular, intraocular, intraarterial, intracerebrospinal, intralesional, or pulmonary routes, or by sustained release systems or an implant. Gene transfer vectors, e.g., for the central nervous system, have been described (see, e.g., Cua, et al. (2001) *J. Immunol.* 166:602-608; Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA). An effective amount of therapeutic will decrease the symptoms typically by at least 10%; usually by at least 20%; preferably at least about 30%; more preferably at least 40%, and most preferably by at least 50%.

V. Kits and Diagnostic Reagents.

This invention provides IL-23 proteins, fragments thereof, nucleic acids, and fragments thereof, in a diagnostic kit. Also provided are binding compositions, including antibodies or antibody fragments, for the detection of IL-23 and IL-23 receptor, and metabolites and breakdown products thereof. Typically, the kit will have a compartment containing either a p19 polypeptide, or an antigenic fragment thereof, a nucleic acid, e.g., a nucleic acid probe or primer. The nucleic acid probe or primer specifically hybridizes under stringent conditions to a nucleic acid encoding p19 or IL-23R.

The kit can comprise, e.g., a reagent and a compartment, a reagent and instructions for use, or a reagent with a compartment and instructions for use. The reagent can comprise p19, the complex of p19 and p40, IL-23R, the complex of IL-23R and IL-12Rbeta1, or an antigenic fragment thereof, a binding composition, or a nucleic acid. A kit for determining the binding of a test compound, e.g., acquired from a biological sample or from a chemical library, can comprise a control compound, a labeled compound, and a method for separating free labeled compound from bound labeled compound.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals (see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162: 2804-2811; Everts, et al. (2002) *New Engl. J. Med.* 168: 883-889). Various assay formats exist, such as radioimmunoassays (RIA), ELISA, and lab on a chip (U.S. Pat. Nos. 6,176,962 and 6,517,234).

This invention provides polypeptides and nucleic acids of IL-23 and IL-23R, fragments thereof, in a diagnostic kit, e.g., for the diagnosis of proliferative conditions, cancer, tumors, and precancerous disorders, e.g., dysplasia.

Also provided are binding compositions, including antibodies or antibody fragments, for the detection of p19, the complex of p19 and p40, IL-23R, the complex of IL-23R and IL-12Rbeta1, and metabolites and breakdown products thereof. Typically, the kit will have a compartment containing either a IL-23 or IL-23R polypeptide, or an antigenic fragment thereof, a binding composition thereto, or a nucleic acid, such as a nucleic acid probe, primer, or molecular beacon (see, e.g., Rajendran, et al. (2003) *Nucleic Acids Res.* 31:5700-5713; Cockerill (2003) *Arch. Pathol. Lab. Med.* 127:1112-1120; Zammatteo, et al. (2002) *Biotech. Annu. Rev.* 8:85-101; Klein (2002) *Trends Mol. Med.* 8:257-260).

A method of diagnosis can comprise contacting a sample from a subject, e.g., a test subject, with a binding composition that specifically binds to a polypeptide or nucleic acid of p19, the complex of p19 and p40, IL-23R, and the complex of IL-23R and IL-12Rbeta1. The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

VI. Uses.

The present invention provides methods for using agonists and antagonists of IL-23 for the treatment and diagnosis of inflammatory disorders and conditions, e.g., neoplastic diseases, cancers, tumors, angiogenesis, precancerous conditions such as dysplasias, anorexia, cachexia, and cancer cachexia, by modulating immune response.

The present invention provides methods of treating or diagnosing a proliferative condition or disorder, e.g., cancer of the uterus, cervix, breast, prostate, testes, penis, gastrointestinal tract, e.g., esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, ganglia, central nervous system (CNS) and peripheral nervous system (PNS), and immune system, e.g., spleen or thymus. The present invention provides methods of treating, e.g., immunogenic tumors, non-immunogenetic tumors, dormant tumors, virus-induced cancers, e.g., epithelial cell cancers, endothelial cell cancers, squamous cell carcinomas, papillomavirus, adenocarcinomas, lymphomas, carcinomas, melanomas, leukemias, myelomas, sarcomas, teratocarcinomas, chemically-induced cancers, metastasis, and angiogenesis. The invention also contemplates reducing tolerance to a tumor cell or cancer cell antigen, e.g., by modulating activity of a regulatory T cell (Treg) (see, e.g., Ramirez-Montagut, et al. (2003) *Oncogene* 22:3180-3187; Sawaya, et al. (2003) *New Engl. J. Med.* 349:1501-1509; Farrar, et al. (1999) *J. Immunol.* 162:2842-2849; Le, et al. (2001) *J. Immunol.* 167:6765-6772; Cannistra and Niloff (1996) *New Engl. J. Med.* 334:1030-1038; Osborne (1998) *New Engl. J. Med.* 339:1609-1618; Lynch and Chapelle (2003) *New Engl. J. Med.* 348:919-932; Enzinger and Mayer (2003) *New Engl. J. Med.* 349:2241-2252; Forastiere, et al. (2001) *New Engl. J. Med.* 345:1890-1900; Izbicki, et al. (1997) *New Engl. J. Med.* 337:1188-1194; Holland, et al. (eds.) (1996) *Cancer Medicine Encyclopedia of Cancer*, 4$^{th}$ ed., Academic Press, San Diego, Calif.).

The present invention provides methods for treating a proliferative condition, cancer, tumor, or precancerous condition such as a dysplasia, with an agonist or antagonist of IL-23, with at least one additional therapeutic or diagnostic agent. The at least one additional therapeutic or diagnostic agent can be, e.g., a cytokine or cytokine antagonist, such as IL-12, interferon-alpha, or anti-epidermal growth factor receptor, doxorubicin, epirubicin, an anti-folate, e.g., methotrexate or fluoruracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, vinca alkaloid, taxane, e.g., paclitaxel and docetaxel, a cell cycle inhibitor, e.g., a cyclin-dependent kinase inhibitor, a monoclonal antibody, a complex of monoclonal antibody and toxin, a T cell adjuvant, bone marrow transplant, or antigen presenting cells, e.g., dendritic cell therapy. Vaccines can be provided, e.g., as a soluble protein or as a nucleic acid encoding the protein (see, e.g., Le, et al., supra; Greco and Zellefsky (eds.) (2000) *Radiotherapy of Prostate Cancer*, Harwood Academic, Amsterdam; Shapiro and Recht (2001) New Engl. J. Med. 344:1997-2008; Hortobagyi (1998) *New Engl. J. Med.* 339: 974-984; Catalona (1994) *New Engl. J. Med.* 331:996-1004; Naylor and Hadden (2003) *Int. Immunopharmacol.* 3:1205-

1215; The Int. Adjuvant Lung Cancer Trial Collaborative Group (2004) *New Engl. J. Med.* 350:351-360; Slamon, et al. (2001) *New Engl. J. Med.* 344:783-792; Kudelka, et al. (1998) *New Engl. J. Med.* 338:991-992; van Netten, et al. (1996) *New Engl. J. Med.* 334:920-921).

The present invention provides methods for the treatment and diagnosis of anorexia and cachexia, including cancer cachexia. Cachexia is a wasting syndrome that occurs in a number of diseases, including cancer, e.g., cancer of the lung and upper gastrointestinal tract. Cachexia occurs in about half of all cancer patients. Diagnosis of cachexia is by a history of substantial weight loss, loss of appetite, and profound weakness, in the context of advanced disease, and muscle wasting (loss of lean body mass). Cytokines, e.g., IL-6, IL-1, TNFalpha, and IFNgamma, have been associated with cachexia (see, e.g., MacDonald, et al., supra; Rubin, supra; Tisdale, supra; Lelli, et al., supra; Argiles, et al., supra).

Also provided are methods of treating extramedullary hematopoiesis (EMH) of cancer. EMH is described (see, e.g., Rao, et al. (2003) *Leuk. Lymphoma* 44:715-718; Lane, et al. (2002) *J. Cutan. Pathol.* 29:608-612).

The gastrointestinal tract comprises, e.g., the lips, mouth, esophagus, stomach, small intestines, appendix, large intestines, colon, anus, and rectum. The respiratory tract comprises, e.g., the trachea, bronchioles, bronchi, lungs, alveoli. The reproductive system includes, e.g., the testes, penis, ovaries, uterus, fallopian tubes. The endocrine system includes, e.g., the pituitary, hypothalamus, pineal gland, thyroid gland, parathyroid, endocrine pancreas, islets, gonads, and adrenal gland.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLES

I. General Methods.

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., N.Y., N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies is described (Coligan, et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology, Vol.* 4, John Wiley, Inc., New York).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila., Pa.; Louis, et al. (2002) *Basic Histology: Text and Atlas*, McGraw-Hill, New York, N.Y.).

Methods for the treatment and diagnosis of cancer are described (see, e.g., Alison (ed.) (2001) *The Cancer Handbook*, Grove's Dictionaries, Inc., St. Louis, Mo.; Oldham (ed.) (1998) *Principles of Cancer Biotherapy*, 3$^{rd}$. ed., Kluwer Academic Publ., Hingham, Mass.; Thompson, et al. (eds.) (2001) *Textbook of Melanoma*, Martin Dunitz, Ltd., London, UK; Devita, et al. (eds.) (2001) *Cancer: Principles and Practice of Oncology*, 6$^{th}$ ed., Lippincott, Phila., Pa.; Holland, et al. (eds.) (2000) *Holland-Frei Cancer Medicine*, B C Decker, Phila., PA; Garrett and Sell (eds.) (1995) *Cellular Cancer Markers*, Humana Press, Totowa, N.J.; MacKie (1996) *Skin Cancer*, 2$^{nd}$ ed., Mosby, St. Louis; Moertel (1994) *New Engl. J. Med.* 330:1136-1142; Engleman (2003) *Semin. Oncol.* 30(3 Suppl. 8):23-29; Mohr, et al. (2003) *Onkologie* 26:227-233).

Software packages and databases for determining, e.g., antigenic fragments, leader sequences, protein folding, functional domains, glycosylation sites, and sequence alignments, are available (see, e.g., GenBank, Vector NTI™ Suite sequence analysis and data management software (Informax, lnc, Bethesda, Md.); GCG Wisconsin Package (Accelrys, Inc., San Diego, Calif.); DeCypher® software package (TimeLogic Corp., Crystal Bay, Nev.); Menne, et al. (2000) *Bioinformatics.* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

II. Mice and Tumor Induction.

IL-23 p19 deficient mice were generated as described in Cua, et al., supra. Mice specifically lacking in IL-23 (p19KO mice; p19 knockout mice; $p19^{-/-}$ mice), $p19^{+/-}$ mice, and $p19^{+/+}$ wild-type control mice, had a B6/129 F2 background.

Skin tumors were chemically induced in either wild-type (wt) or IL-23 deficient mice (p19KO mice). Tumors were initiated using 50 micrograms of 7,12-dimethylbenz[a]anthracene (DMBA) followed by a promotion steps consisting of two treatments of 30 micrograms each of TPA per week (see, e.g., Oft, et al. (2002) *Nat. Cell. Biol.* 4:487-494).

With tumor studies with Ep2X1B1-nu/nu mice, tumors metastasize, while cachexia does not occur. The mice die, e.g., from extramedullary hematopoiesis (EMH). With tumor studies with Ep2XB1-Balb/c mice, tumor metastasis does not occur, apparently because of the intact immune system in these mice.

III. Expression of Subunits of p19 and IL-23R.

Expression of the p19 subunit of IL-23 and the IL-23R subunit of IL-23 receptor was elevated in a number of cancers, tumors, and cell lines, e.g., cancer of the gastrointestinal tract, reproductive tract, skin, and breast (Table 1).

Table 1. Expression of subunits of p19 and IL-23R by Taqman® real time quantitative PCR analysis, relative to ubiquitin (1 .0). The values are from diseased and adjacent normal tissues, where indicated.

TABLE 1

Expression of subunits of p19 and IL-23R by Taqman ® real time quantitative PCR analysis, relative to ubiquitin (1.0). The values are from diseased and adjacent normal tissues, where indicated.

| Expression of human p19 | | | |
|---|---|---|---|
| normal colon, adjacent | 4.8 | colon stage I, adenocarcinoma | 30.5 |
| normal colon, adjacent | 2.0 | colon stage II, adenocarcinoma | 73.4 |
| normal colon, adjacent | 0.8 | colon stage II, adenocarcinoma | 18.1 |
| normal colon, adjacent | 0.21 | colon stage III, adenocarcinoma | 34.0 |
| normal skin adjacent | 2.2 | human skin II melanoma | 21.8 |
| normal skin adjacent | 6.7 | human skin II nodular melanoma | 16.4 |
| normal skin adjacent | 8.4 | human skin II nodular melanoma | 26.8 |
| normal skin adjacent | 9.3 | human skin II superficial spreading melanoma | 75.1 |
| uterus adjacent | 1.6 | ovary papillary serous cystadenocarcinoma | 55.0 |
| ovary adjacent | 1.9 | ovary papillary serous cystadenocarcinoma | 17.7 |
| breast adjacent | 8.2 | breast IIB carcinoma, medullary | 32.0 |
| breast adjacent | 0.6 | breast IIA carcinoma, infiltrating duct | 3.1 |
| breast adjacent | 0.2 | breast IIA carcinoma, infiltrating duct | 3.9 |

TABLE 1-continued

Expression of subunits of p19 and IL-23R by Taqman ® real time quantitative PCR analysis, relative to ubiquitin (1.0). The values are from diseased and adjacent normal tissues, where indicated.

| Expression of human IL-23R | |
|---|---|
| monocyte/PBMC resting | 10.0 |
| leukocytes leukemia SR cell line | 415.8 |
| leukocytes leukemia K562 cell line | 396.7 |
| leukocytes leukemia MOLT-4 cell line | 0.0 |
| leukocytes leukemia HL60 TB cell line | 374.1 |

RNA from tissues or cell pellets was extracted using RNeasy® columns (Qiagen, Valencia, Calif.) and treated with Dnase I (Promega, Madison, Wis.). cDNA were prepared and used as templates for quantitative real time PCR. cDNA (25 ng) was analysed for expression of a range of genes using GeneAmp® 5700 Sequence Detection System (Applied Biosystems, Foster City, Calif.). Analysis of cDNA samples from normal and tumor colon and ovary tissue was normalized to expression of the housekeeping gene, ubiquitin.

IV. p19 Antagonists Prevent or Reduce Tumors.

Tumors induced by injected tumor cells or by chemical carcinogenesis, were eradicated or reduced in mice treated antagonists to IL-23, e.g., by treatment with anti-p19 antibody, or by genetic ablation of the p19 subunit (p19KO). p19 is a subunit of IL-23 only, while p40 is a subunit of both IL-23 and IL-12. In contrast, treatment with an IL-12, under some conditions, exacerbated tumors, i.e., resulted in an increase in tumor volume, relative to control mice.

Tumors in mice resulted in cancer, cancer cachexia, extramedullary hematopoiesis, and death. Treatment of tumor-bearing Balb/c mice with anti-p19 antibody resulted in a halt to increases in tumor volume, while treatment with anti-p40 antibody provoked weight gain of the animal, likely a reversal of cachexia, but an increase in tumor volume (Table 2).

TABLE 2

Tumor growth in Balb/c mice inoculated with Ep2 (a.k.a. XTb cells) cancer cells (ras-transformed mouse mammary cells).

| | Tumor size (mm$^3$) | | |
|---|---|---|---|
| Antibody treatment | Day 1 | Day 11 | Day 21 |
| Isotype antibody (8D5) | 0 mm$^3$ | 225 mm$^3$ | 500 mm$^3$ |
| Anti-p19 antibody (29A2) | 0 | 200 | 250 |
| Anti-p40 antibody (C17.8) | 0 | 250 | 1150 |

Cancer death and cancer cachexia were induced in mice, where death and weight loss were prevented by anti-p40 antibody. Mice were injected with $1 \times 10^6$ EpXT tumor cells (s.c.). Tumor bearing nude mice (Ep2XB1 nu/nu) died from lethal lung metastasis, with deaths occurring at from days 22-42 after the injection. Tumor bearing Exp2XB1 Balb/c mice died at about days 22-49 after the injection, where the BalbC/c mice died in absence of lung metastasis. Cachexia was indicated by the decrease in body weight occurring (prior to death). Progressive weight loss occurred, starting at about day 16. The initial weight, at day 1 was 22-23 grams, while the weight at death was in the range of 16-18 grams.

Antibody treatment was with C17.8 rat anti-p40 antibody (1 mg/week). With antibody treatment, the Ep2XB1-Balb/C mice (immunocompetent mice), survived until about day 64, after which deaths occurred until day 85. Anti-p40 antibody treatment also resulted in a maintenance of body weight (at about 17 grams) in half of the mice, with a progressive increase in body weight of the remaining mice, to a maximum, within the time frame of the experiment, of 22-23 grams. Thus, anti-p40 antibody resulted in improvement in health, according to survival time and regain of body weight, though anti-p40 could also result in a decline in health, as shown by an increase in tumor size (Table 2).

Cancer was chemically induced by treatment with DMBA (50 micrograms) and 2×30 micrograms tetradecanoylphorbol-13-acetate (TPA) per week (Gschwendt, et al.(1991) *Trends Biochem Sci.* 16:167-169). Chemical carcinogenesis treatments were applied to B6/129 wild type mice and to p19KO mice. Wild type mice readily developed tumors but the p19KO mice did not acquire tumors (Table 3).

TABLE 3 p19KO Mice Resist Chemical Carcinogenesis.

|  | Initiation with DMBA (50 micrograms); Promotion with TPA (2 × 30 micrograms/week for 13 weeks). | | Initiation with DMBA (50 micrograms); Promotion with TPA (2 × 30 micrograms/week for 20 weeks). | |
| --- | --- | --- | --- | --- |
|  | First tumor occurrence (after TPA) | Tumor number per mouse | First tumor occurrence (after TPA) | Tumor number per mouse |
| B2/129 wild type mouse | 8 weeks | 11 | 8 weeks | 8 |
| p19KO mouse | None found in examined time frame. | 0 | None found in examined time frame. | 0 |

Separate studies demonstrated that the p19KO prevented tumor formation, while the p35KO exacerbated tumor formation (Table 4).

TABLE 4

Influence of p19KO versus p35KO on chemical carcinogenesis.

|  | Average number of tumors per mouse |
| --- | --- |
| C57/129 wild type | 10.0 |
| p19KO (C57/129) | 0.0 |
| C57B/6 wild type | 4.5 |
| p35KO (C57/129) | 11.0 |

Tissue and cell expression of the subunits of IL-23 and subunits of IL-12 was determined, after carcinogen treatment. DMBA alone, TPA alone, and DMBA with TPA, induced expression of the p19 subunit of IL-23, these chemicals was applied to the mouse's back. For example, two days after treatment with DMBA resulted in an increase in p19 expression from 1.5 (untreated) to 6.3 (at t=2 days). Expression of p40 increased, but was relatively low in this time interval (0.1 untreated; 0.4 at t=2 days). Five hours after treatment with TPA resulted in an increase in p19 expression (2.5 control; 15.5 with TPA treatment), but relatively little change in p40 expression (2.0 control; 3.5 with TPA treatment). Five hours after treatment with DMBA plus TPA resulted in large increases in p19 expression (6.0 control; 32.0 DMBA+TPA), but moderate levels of p40 expression (2.0 control; 4.0 DMBA+TPA).

Response of human keratinocytes to, e.g., DMBA, TPA, and lipopolysaccharide (LPS), was also determined (Table 5). TPA specifically induced p19, with little or no induction of p40, the common subunit of IL-23 and IL-12. LPS induced p19, indicating a role in IL-23 in innate response. Toll-like receptors that bind LPS occur on keratinocytes (see, e.g., Song, et al. (2002) *J. Invest. Dermatol.* 119:424-432). Etoposide is an anti-cancer agent that inhibits topoisomerase II and induces apoptosis (see, e.g., Robertson, et al. (2000) *J. Biol. Chem.* 275:32438-32443; Karpinich, et al. (2000) *J. Biol. Chem.* 277:16547-16552).

TABLE 5

Response of Human Keratinocytes to Various Additives.

| Additive | p19 | p40 | p35 | EBI3 subunit of IL-27 (p28 + EBI3) |
| --- | --- | --- | --- | --- |
| Control | 1.1 | N.D. | 0.4 | 0.01 |
| DMBA | 1.0 | N.D. | N.D. | N.D. |
| TPA | 1.9 | N.D. | 0.2 | 1.25 |
| LPS | 4.45 | 0.05 | 0.35 | 0.25 |
| Etoposide | 2.5 | 0.4 | 1.75 | 0.6 |

N.D. means not detected.

Anti-p19 antibodies were tested for their effect on the 4T1 mouse breast cancer cell model. Mice were treated with control mIgG1 (27F11) antibody or with anti-p19 antibody (29A2). Tumor growth was monitored on days 1, 3, 4, 5, 6, 7, 8, 9, 10, and 11. Antibodies (1 mg/dose) were administered on days 2, 5, 8, and 10. On day 4, the tumor size of the control antibody treated mouse was about 175 mm$^3$, while tumor size of the anti-p19 antibody treated mouse was about 135 mm$^3$. Thus, anti-p19 antibody is effective in treating a model of breast cancer. After day 4, tumors in both groups grew at about the same rate, indicating that the antibody dose was not sufficient to counteract the IL-23 expressed by the tumor at later periods in time.

Histology of the Ep2 mouse breast cancer model demonstrated co-localization of IL-23R and NK cells, as determined by staining for p19, which resides bound to IL-23R, and by staining for CD49B, a marker for NK cells. This co-localization occurred in the central part of the tumor, i.e., in the necrotic region. Histology of the Ep2 mouse breast cancer also demonstrated co-localization of p19 and T cells. T cell location was determined by staining for CD3. This co-localization occurred at the peripheral part of the tumor.

V. Listing of Sequence Identifiers

SEQ ID NO: 1 is human IL-23p19 nucleic acid sequence.
SEQ ID NO: 2 is human IL-23p19 amino acid sequence.
SEQ ID NO: 3 is mouse IL-23p19 nucleic acid sequence.
SEQ ID NO: 4 is mouse IL-23p19 amino acid sequence.
SEQ ID NO: 5 is human IL-23 receptor nucleic acid sequence.
SEQ ID NO: 6 is human IL-23 receptor amino acid sequence.
SEQ ID NO: 7 is human IL-12Rbeta1 amino acid sequence.
SEQ ID NO: 8 is human IL-12 p40 amino acid sequence.
SEQ ID NO: 9 is mouse L-12 p40 amino acid sequence.
SEQ ID NO: 10 is mouse IL-23 hyperkine
SEQ ID NO: 11 is human IL-23 hyperkine.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of inhibiting tumor growth comprising contacting a tumor cell with an effective amount of a binding composition comprising an antigen-binding site of an antibody that specifically binds to a polypeptide comprising residues 1-168 of SEQ ID NO:2.

2. The method of claim 1, wherein the tumor cell expresses IL-23.

3. The method of claim 1, wherein the binding composition comprises:
   a) a polyclonal antibody;
   b) a monoclonal antibody;
   c) a humanized antibody, or a fragment thereof; or
   d) an Fab, Fv, or F(ab')₂ fragment.

4. The method of claim 1, wherein the tumor cell is:
   a) a colon cancer cell;
   b) an ovarian cancer cell;
   c) a breast cancer cell; or
   d) a melanoma cell.

5. A method of treating a subject suffering from a cancer or tumor comprising administering to the subject an effective amount of a binding composition comprising an antigen-binding site of an antibody that specifically binds to a polypeptide comprising residues 1-168 of SEQ ID NO:2.

6. The method of claim 5, wherein the binding composition inhibits:
   a) growth of the cancer or tumor;
   b) cachexia;
   c) anorexia; or
   d) angiogenesis.

7. The method of claim 5, wherein the binding composition comprises:
   a) a polyclonal antibody;
   b) a monoclonal antibody;
   c) a humanized antibody, or a fragment thereof; or
   d) an Fab, Fv, or F(ab')₂ fragment.

8. The method of claim 5, wherein the cancer or tumor is of the:
   a) gastrointestinal tract;
   b) respiratory tract;
   c) reproductive system; or
   d) endocrine system.

9. The method of claim 5, wherein the cancer or tumor is:
   a) colon cancer;
   b) ovarian cancer;
   c) a melanoma; or
   d) breast cancer.

10. A method of inhibiting tumor growth comprising contacting a tumor cell with an effective amount of a binding composition comprising an antigen-binding site of an antibody that specifically binds to a polypeptide comprising the sequence of SEQ ID NO: 2.

11. A method of treating a subject suffering from a cancer or tumor comprising administering to the subject an effective amount of a binding composition comprising an antigen-binding site of an antibody that specifically binds to a polypeptide comprising the sequence of SEQ ID NO: 2.

* * * * *